(12) United States Patent
Thomeczek et al.

(10) Patent No.: US 7,645,211 B1
(45) Date of Patent: Jan. 12, 2010

(54) PERSONAL AGILITY DEVELOPER (75) Inventors: Lauren Thomeczek, Fishers, IN (US);
Shawn Pletch, Leganon, IN (US);
James S. Hutchison, Indianapolis, IN (US)

(73) Assignee: Lauranzo, Inc., Fishers, IN (US)

( * ) Notice: Subject to any disclaimer, the term of this patent is extended or adjusted under 35 U.S.C. 154(b) by 542 days.

(21) Appl. No.: 11/279,939

(22) Filed: Apr. 17, 2006

(51) Int. Cl.
*A63B 71/00* (2006.01)
(52) U.S. Cl. ............... 482/1; 482/8; 482/9; 482/900
(58) Field of Classification Search ............... 482/1–9, 482/81, 900–902; 434/247, 250
See application file for complete search history.

(56) References Cited

U.S. PATENT DOCUMENTS

| | | | |
|---|---|---|---|
| 3,749,810 A | 7/1973 | Dow | |
| 4,176,471 A | 12/1979 | Roe | |
| 5,947,478 A | 9/1999 | Kwan et al. | |
| 6,336,891 B1 | 1/2002 | Fedrigon et al. | |
| 6,447,427 B1 | 9/2002 | Myrland et al. | |
| 6,450,886 B1 | 9/2002 | Oishi et al. | |
| 6,634,994 B2 * | 10/2003 | Reid et al. | 482/81 |
| 6,743,971 B1 | 6/2004 | Chen | |
| 6,916,273 B2 | 7/2005 | Couvillion, Jr. et al. | |
| 7,060,000 B2 * | 6/2006 | Carlson | 482/1 |
| 7,513,852 B2 * | 4/2009 | Wilkins et al. | 482/8 |
| 2001/0005692 A1 | 6/2001 | Song | |
| 2002/0019258 A1 | 2/2002 | Kim et al. | |
| 2002/0183961 A1 * | 12/2002 | French et al. | 702/150 |
| 2005/0014113 A1 | 1/2005 | Fleck et al. | |
| 2005/0233862 A1 | 10/2005 | Madigan et al. | |
| 2005/0255914 A1 | 11/2005 | McHale et al. | |

FOREIGN PATENT DOCUMENTS

| | | |
|---|---|---|
| JP | 2002085618 A | 3/2002 |
| JP | 2003038696 A | 2/2003 |
| JP | 2005021595 A | 1/2005 |
| WO | WO 2005/010795 A1 | 2/2005 |

* cited by examiner

*Primary Examiner*—Glenn Richman (57) ABSTRACT

An electronic agility training system, including an array of multilayer, flexible footfall portions, a microprocessor operationally connected footfall portions, a user interface connected to the microprocessor, a pressure sensor positioned in each respective footfall portion and connected to the microprocessor, and a light source positioned in each respective footfall portion and operationally connected to the microprocessor. The microprocessor is programmed to receive user information and to sequentially light respective footfall portions in one of a plurality of predetermined patterns and speeds. Actuation of the pressure sensor positioned in a lit footfall portion generates a first signal to the microprocessor, while actuation of the pressure sensor positioned in an unlit footfall portion generates a second signal. Likewise, a null activation of the pressure sensor positioned in a lit footfall portion generates a second signal to the microprocessor. The microprocessor counts the respective first and second signal received and generates a score based thereupon.

14 Claims, 5 Drawing Sheets

PERSONAL AGILITY DEVELOPER

TECHNICAL FIELD

The following relates generally to sporting equipment and, more particularly, to an electronic device for guiding an athlete through a series of footfalls and evaluating and displaying the athlete's performance of the same.

BACKGROUND

Agility is a key prerequisite of athletes competing in most, if not all, sports. One means of sharpening one's agility is the training ladder. As its name suggests, in its most basic form, the training ladder is simply a ladder-like matrix of spaces laid out on the ground for an athlete to run through. Unlike ladders for climbing, the training ladder is usually, although not always, defined by a series of ropes or other flexible members connected together to define a two-dimensional matrix of spaces for the athlete to run through. Typically, the athlete attempts to run through the matrix as fast as possible without fouling the ropes defining the spaces. Agility is sharpened by running the course at increasing speeds.

Traditional training ladders do have several drawbacks. Firstly, such ladders to not teach patterns to the user, as the athlete must be shown each individual pattern to be run and memorize the same in order to later practice the pattern. Consequently, rope ladders cannot be used to challenge an athlete's reflexes by varying the run pattern in real time. Thus, athletes training on a traditional training ladder may develop muscle memory for a specific course that does not translate into more generalized agility. Likewise, developing speed for a single, defined set of movements will not, past a certain point, translate into increasing agility for other sets of movements.

Also, athletes attempting to increase their speed on an agility-training course require a second party to time them. It is a practical impossibility for an athlete to concentrate on timing themselves, even with the aid of a stopwatch, while trying to focus on shaving time measured in the tenths of seconds from a previous best time.

Further, athletes running a rope-based training ladder often misstep and catch one of the ropes with their feet. When this happens, the rope ladder is often pulled and distorted, requiring the athlete to stop and relay the training ladder. Also, rope ladders tend to become tangled during storage, requiring time and effort to sort out prior to deployment. This tangling tendency also makes rope ladders more difficult to transport. Further, the propensity for an athlete to catch his foot on the rope ladder constitutes an unnecessary tripping and falling hazard. Moreover, current ladders cannot communicate with one another and track all scores on a central device, so a team must use one ladder at a time. All team members must memorize individual scores as they go along.

In addition, it is difficult to ascertain when an athlete missteps when running a rope ladder, unless the athlete actually becomes entangled therein. Errors made when running rope ladders must be observed, thus requiring a third party observer to accurately view and record errors. Also, rope ladders do not provide feedback regarding run speed o and/or accuracy; a third party observer is likewise required to provide them. Finally, rope ladders cannot be used in the dark.

Thus, there is a need for an agility training mechanism that teaches patterns to the user, provides a visual aid, communicates with other devices and records results, does not require a second party for timing, feedback and/or error reporting, and is not easily fouled and distorted and/or does not present a tripping hazard. The present technology addresses these needs.

SUMMARY

The portable agility-training device typically includes a number of layers. Some of these may include a flexible base layer, a flexible, non-conducting electronics-mounting layer, an impact-absorbent layer, and a flexible top layer. The top layer typically includes grid markings defining an array of footfall portions. Pressure sensors and light sources are positioned in the electronics-mounting layer and positioned to coincide with the respective footfall portions.

One object of the present technology is to provide an improved system for measuring and improving agility. Related objects and advantages of the present technology will be evident from the following descriptions.

DETAILED DESCRIPTION OF THE PREFERRED EMBODIMENTS

For the purposes of promoting an understanding of the principles of what is claimed and presenting the currently understood best mode of operation, reference will now be made to the embodiments illustrated in the drawings and specific language will be used to describe the same. It will nevertheless be understood that no limitation of scope is thereby intended, with such alterations and further modifications in the illustrated device and such further applications of the principles as illustrated therein being contemplated as would normally occur to one skilled in the relevant art.

Figure 1:
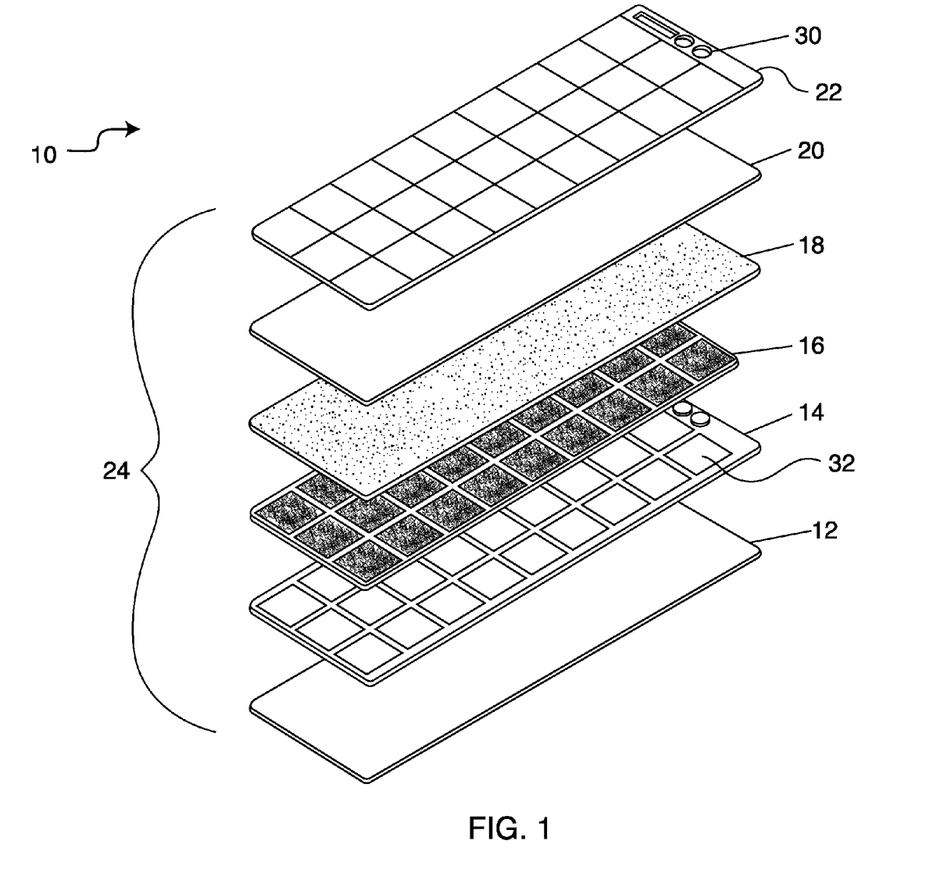
FIG. 1 is an exploded perspective view of a first embodiment personal agility-training device.
Figure 2:
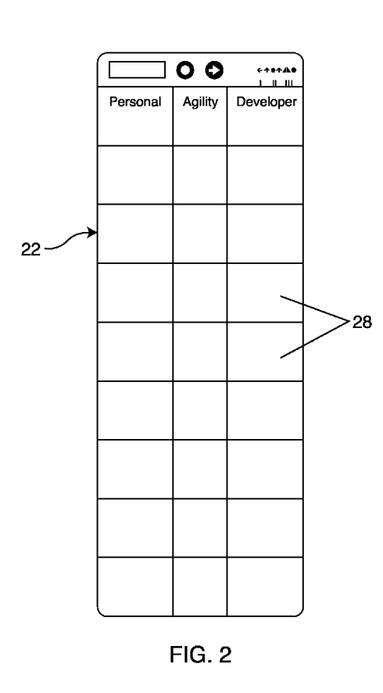
FIG. 2 is a top plan view of the device of FIG. 1.
Figure 3:
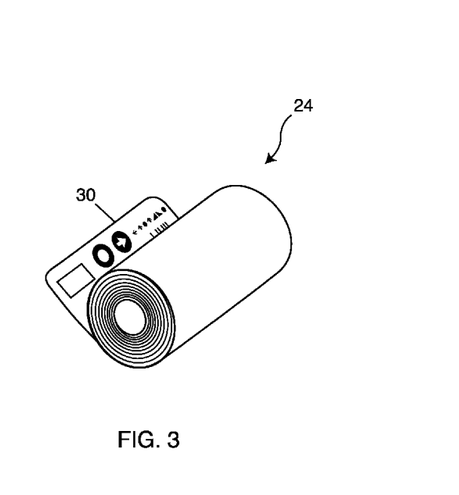
FIG. 3 is a perspective view of the device of FIG. 1 rolled into a storage configuration.

A first embodiment of an agility-training device 10 is illustrated in FIGS. 1-3. The device 10 typically includes (listed from the bottommost layer up) a base layer 12, an electrical circuit layer 14, a separation layer 16, an impact absorbing protection layer 18, a transparent cover layer 20, and a soft top display layer 22. The layers 12, 14, 16, 18, 20, 22 are typically fastened or sealed together as a unitary flexible member or mat 24. The mat 24 is more typically sufficiently flexible as to be rollable into a cylinder for storage and easy transport (see FIG. 3). The top layer 22 is typically marked with a grid 26 to delineate separate and distinct footfall portions 28 and is also typically marked (more typically at one end) to denote user interface or control pad portions 30. The footfall and user interface/control pad portions 28, 30 are typically aligned with light sources, pressure sensors and/or switches 32 positioned on the circuit layer 14.

Figure 4:
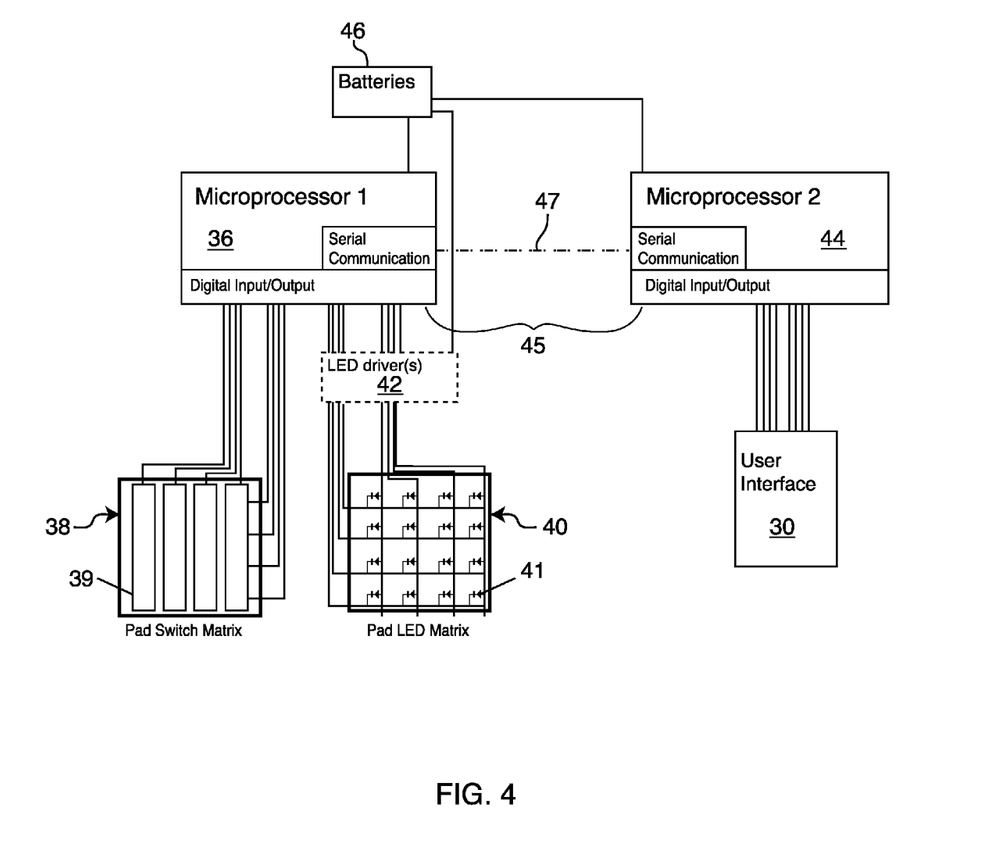
FIG. 4 is a schematic diagram of the electric circuit portion of the device of FIG. 1.

FIG. 4 schematically illustrates the device 10. A first microprocessor 36 is connected in electric communication with a sensor or switch matrix 38 operationally connected to the electric circuit layer 14. The individual sensors/switches 39 in the matrix 38 may be piezoelectric, capacitance based, resistance based, optical and/or acoustic (i.e., use optical and/or microphonic triangulation), or the like. The first microprocessor 36 is likewise connected in electric communication with a light source matrix 40 likewise operationally connected to the electric circuit layer 14. Typically, the two matrices 38, 40 substantially overlap, each with at least one sensor/switch 39 and light source 41 positioned in each footfall portion 28. The light sources 41 are typically light emitting diodes (LEDs), but may be of any convenient type, such as electroluminescent panels or the like. Typically, a set of drivers 42 is electrically connected between the light source matrix 40 and the microprocessor 36.

A second microprocessor 44 is connected in electric communication with the first microprocessor 36 and with the user interface 30. The user interface 30 typically includes a plurality of switches/sensors and a plurality of visual feedback displays positioned such that programming of the microprocessor 44 may be accomplished by actuation of the appropriate sensor(s) 46 via foot pressure, with feedback from the microprocessor energizing the appropriate displays 48. Both microprocessors 36, 44 are electrically connected to a power source 46. The power source 46 may be a set of batteries, a transformer connected to line current, a set of solar cells, or the like.

Typically, the first and second microprocessors 36, 44 are linked in electric communication, such as by a serial communication bus 47, and may be envisioned to cooperate as a microprocessor assembly 48. Alternately, the microprocessor assembly 48 may include more (or fewer) microprocessor units. Typically, however it is configured, the microprocessor assembly 48 performs the functions detailed herein and attributed to first and second microprocessors 36, 44.

Figure 5:
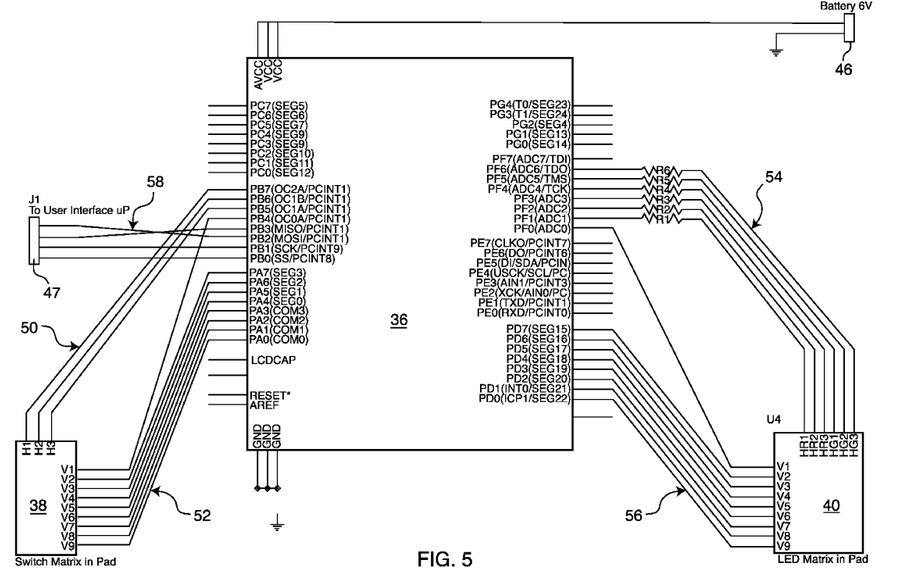
FIG. 5 is detailed schematic diagram of the connections to the first microprocessor of FIG. 4.
Figure 6:
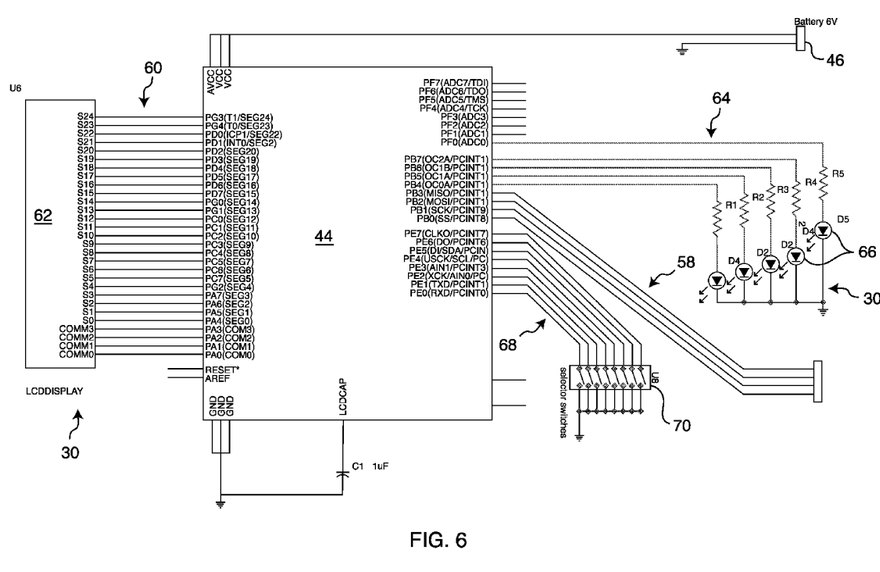
FIG. 6 is detailed schematic diagram of the connections to the second microprocessor of FIG. 4.

FIGS. 5 and 6 schematically illustrate the wiring of one typical embodiment of the device 10. As shown in FIG. 5, the first microprocessor 36 includes a first and a second set of electrical connections or leads 50, 52 extending therefrom to connect to the switches 39 defining the switch matrix 38. The sets of leads 50, 52 define an m×n matrix, with one set 50 having n leads and the other set 52 including m leads, where m and n are non-zero positive integer numbers. The product of m and n equals the number of switches 39 in the array 38. For example, m may be three and n may be nine, thus connecting to twenty-seven discrete switch locations defining the switch matrix 38.

Likewise, a third and a fourth set of electrical connections or leads 54, 56 extend from the microprocessor 36 to connect to the discrete light sources 41 defining the lighting display matrix 40. The sets of leads 54, 56 define another m'×n' matrix, with one set 54 having n' leads and the other set 56 including m' leads, where m' and n' are again non-zero positive integer numbers. The product of m' and n' equals the number of light sources 41 in the array 40. Typically, m' and n' have identical values to m and n as defined above, respectively.

The first microprocessor 36 further maintains communication with the second microprocessor 44, such as by a number of electrical connections 58 extending therebetween. Alternately, the two microprocessors 36, 44 may be in wireless communication with each other or the like. Further, the microprocessor is electrically connected to the power source 46.

Turning to FIG. 6, it can be seen that a plurality of leads 60 extend between the second microprocessor 44 and a liquid crystal display portion 62 of the user interface 30. Likewise, a plurality of leads 64 extends between the microprocessor 44 and a plurality of light sources (such as LCDs) 66, with each respective lead of the plurality 64 connected to a respective light source of the plurality 66. Further, another plurality of leads 68 extends between the microprocessor and a plurality of selector switches 70, with each respective lead connecting to a respective switch of the plurality 70.

Typically, the number of interconnecting wires required may be minimized by selecting LEDs as the light sources 41 and organizing the LEDs 41 into a rectangular m×n LED matrix array 40 (where m denotes the number of horizontal positions and n is the number of vertical positions); such an array 40 is energized as an m×n array using m+n wires. The electrical connection at each vertex is provided by the LED 41. All interconnection is thus to digital outputs from the microprocessor 36. Any particular LED 41 may be energized by choosing the appropriate m to be "high" and the appropriate "n" to be low. Thus, any desired LED 41 may be reliably lit as desired.

In some embodiments, it may be advantageous, if more than one LED 41 is desired to be emitting at any one time, to flash the chosen LEDs 41 sequentially at a high speed. To do this, each of the "n" vertical lines may be brought low in sequence and each desired "m" line energized at the appropriate time in the sequence. In order to give the illusion of uniform and constant illumination, the complete sequential scan of all "n" lines is typically completed with a frequency greater than the "flicker fusion" frequency of the human eye (i.e., greater than about ~30 Hz). The current supplied to the respective LEDs 41 during a "pulse" can be quite high and the perceived illumination brightness is not diminished by this technique. However these high currents will typically require use of dedicated circuitry 42 to drive the LEDs 41, because of typical microprocessor power limitations.

Because the LED 41 is a diode and conducts in only the "forward" direction, it is also be possible to further reduce the number of wires by 2. At each vertex (intersection of horizontal and vertical wire) one can attach a "forward" LED 41 and a "backward" LED 41. For instance, two different colors could be chosen for a given location (there are even bicolor LEDs available in a single package wired this way). To utilize this arrangement, the sequence above would be concatenated with one of opposite polarity, where each of the "n" vertical lines can be brought high in sequence and each desired "m" line brought low at the appropriate time in the sequence. This would light the desired "backward" wired LEDs 41 in sequence after the "forward" wired LEDs 41 were lit in sequence.

Likewise, the number of switching interconnecting wires required may be minimized by organizing the switches 39 as a rectangular m×n switch matrix array 38 (where m denotes the number of horizontal positions and n is the number of vertical positions); such an array 38 may be interrogated as an m×n array using m+n wires. This arrangement also facilitates construction because each pressure switch location may typically correspond to a section of horizontal contact surface separated from a horizontal contact surface by a perforated piece of foam. Pressure on that segment causes the two contacts 39 to make electrical contact through the perforations.

To assure complete decoding for arbitrary number of switch closings the following technique is typically used for attachment to the microprocessor 36. The m horizontal positions are typically connected to digital inputs, and the n vertical positions connected to digital outputs normally high. The n outputs will be sequentially brought low in turn and each of the m inputs interrogated. In such a way the entire m×n switch matrix can be characterized. This method allows complete decoding of arbitrary keypad inputs. The sequence is typically completed at a frequency high enough to detect the fastest discerned movement.

In operation, the device 10 is set in place and the microprocessors 36, 44 are energized. Typically, a short setup routine requests specification of the light sequencing and performance reporting. The athlete is expected to step as indicated by which footfall portion 28 is characterized by an energized light source 41 located therein. The lighting sequence is initiated, and the subject athlete's footfalls are recorded. The footfalls are recorded using a pressure sensitive switch 39 connected via flexible conductors to the microprocessor 36. Similarly the LEDs 41 are embedded in the layers 24 and energized via flexible conductors connected to the microprocessor 36. A competency score is calculated, stored and/or reported.

Typically, the device 10 offers a number of predetermined patterns for the athlete to run, and more typically, is configured to generate 'random' run patterns of sequentially progressing target footfall portions 28 to further challenge the athlete's reflexes. Likewise, the device 10 is typically configured to offer a number of selectable predetermined run speeds, and more typically may be operated to randomly vary the run speeds. Such patterns and speeds (and their combinations) may be sorted and grouped by 'skill levels', such that beginner athletes may operate the device at speeds and patterns less challenging 'skill levels' while veteran athletes have the opportunity of using faster speeds and/or more complex training patterns to better hone agility.

Typically, an athlete may use the device 10 to measure and/or increase their agility as follows. First, the athlete inputs user identification information into the microprocessor assembly 48 through the user interface 30. The microprocessor assembly 48 then sequentially lights, for a predetermined period of time, respective footfall portions 28 in a predetermined pattern (one of many available which may be chosen by the user or selected at random by the microprocessor assembly 48) and at a predetermined speed (again, one of many available which may be chosen by the user or selected at random by the microprocessor assembly 48). A 'correct' signal is typically generated and sent to the microprocessor assembly 48 each time a pressure sensor 39 positioned in a lit footfall portion 28 is actuated. An 'error' signal is likewise typically generated and sent to the microprocessor assembly 48 each time a pressure sensor 39 positioned in an unlit footfall portion 28 is actuated and for each time a pressure sensor 39 positioned in a lit footfall portion 28 remains unactuated for the entire predetermined period of time during which the footfall portion 28 is lit; although a misstep will thus generate an 'error' signal, the device 10 is not disturbed by a misstep (i.e., the athlete will not 'catch her feet' as she might if using a ladder) and thus it is not necessary for the athlete to stop and reposition the device 10. The microprocessor assembly 48 then typically counts the number of respective 'correct' and 'error' signals generated during the training exercise and generates a score for the user based on the number of 'correct' and 'error' signals received. The microprocessor 48 then typically assigns a sequencing index (typically a time and date stamp) to the score and stores the so-indexed score in memory. If desired, the microprocessor assembly 48 may then compare sequential stored scores for a given user and calculate a progress value and/or generate a progress graph for that user from the compared scores.

Further, after a second user has inputted his/her information and completed at least one training exercise as outlined above, the microprocessor assembly 48 may compare respective first and second user scores and rank the first and second users based on compared first and second user scores, calculate and compare the progress of each respective user, or the like. This process may be likewise completed for a plurality of users, such as members of a team, to generate training information useful to identify underperformers, athletes in need of extra training, or the like.

Typically, the device incorporates two microprocessors 36, 44 connected together in electric communication 58, such as via a standard serial communication bus 47 or wirelessly. One of these microprocessors 36 is typically dedicated to driving light sequences and recording footfall events in the device 10 while the other microprocessor 44 typically controls the user interface 30. However, the tasks may be split between the microprocessors 36, 44 as desired. Typically, dual microprocessor 36, 44 architecture allows an adequate number of ports to accommodate sufficient numbers of footfall portions 28 using fairly low density packaging while also facilitating the operation of multiple devices 10 from one user interface 30. Thus, multiple devices 10, perhaps separated by some distance, may be linked to provide a more comprehensive and varied workout for one or a plurality of athletes.

In some alternative embodiments, a plurality of devices 10 are linked (i.e., 'daisy-chained') such that a number of athletes may simultaneously train or one athlete may utilize a more challenging extended training route comprised of plural connected devices 10. Likewise, speakers (not shown) may be connected to the microprocessors 36, 44 so that sounds may be associated with the flashing lights or even used instead of flashing lights. Likewise, the lights from the light sources 41 may be conveyed to the footfall portions 28 via optical fibers (not shown), or the light sources 41 may be attached to a flexible circuit board (not shown).

In other alternative embodiments, the user interface 30 and/or one or both microprocessors 36, 44 are remotely located from the mat 24; in these embodiments, the remote portions 30, 36, 44 are in remote communication (such as by radio, infrared, ultrasound, or the like) with the pad portions 24 of one or more devices 10. For example, several pad portions 24 may be linked to a user interface 30 and a microprocessor 36, 44 defining a control box via radio; the control box 30, 36, 44 may be operated by a central person, such as a coach, to more directly guide the training of several members of a team.

While the technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nearly infinite number of insubstantial changes and modifications to the above-described embodiments and that it would be impractical to attempt to describe all such embodiment variations in the present specification. Accordingly, it is understood that all changes and modifications that come within the spirit of the claims are desired to be protected.

We claim:
1. A portable electronic agility training device, comprising:
an array of spaced pressure sensors;
an array of light emitters;
a first electronic controller operationally connected to the array of spaced pressure sensors and operationally connected to the array of light emitters;
a user interface;
a second electronic controller operationally connected to the user interface and connected in electric communication to the first electronic controller; and
a power source operationally connected to the first and second electronic controllers;

wherein each respective pressure sensor defining the array of spaced pressure sensors is paired with a respective light emitter;
wherein the first electronic controller sequentially energizes the respective light emitters for a finite energization period;
wherein actuation of the pressure sensor paired with an energized light emitter during the energization period generates a 'correct' signal to the second electronic controller;
wherein actuation of the pressure sensor paired with an energized light emitter outside of the energization period generates an 'error' signal to the second electronic controller;
wherein a null signal received from a pressure sensor paired with an energized light emitter during the energization period generates an 'error' signal to the second electronic controller; and
wherein actuation of a pressure sensor not paired with an energized light emitter generates an 'error' signal to the second electronic controller.

2. The device of claim 1, wherein respective 'error' and 'correct' signals are counted and stored.

3. The device of claim 2 wherein a microprocessor generates a score based on the respective counted 'error' and 'correct' signals.

4. The device of claim 1 wherein user information is inputted into a microprocessor.

5. The device of claim 4 wherein respective 'error' and 'correct' signals are counted and stored; wherein a microprocessor generates a score based on the respective counted 'error' and 'correct' signals; wherein the score is associated with the user information; and wherein the score is stored in the microprocessor.

6. The device of claim 5 wherein the microprocessor calculates the progress of a user over time from sequentially stored scores.

7. Wherein the first and second electronic controllers are connected in radio communication.

8. An electronic agility training device, comprising:
an array of multilayer, flexible footfall portions;
a microprocessor assembly operationally connected to the array of multilayer, flexible footfall portions;
a user interface operationally connected to the microprocessor assembly;
at least one pressure sensor positioned in each respective footfall portion and operationally connected to the microprocessor assembly;
at least one light source positioned in each respective footfall portion and operationally connected to the microprocessor assembly;
wherein the microprocessor assembly is programmed to receive user information from the user interface;
wherein the microprocessor assembly is programmed to sequentially energize the light sources to light respective footfall portions in one of a plurality of predetermined patterns and at one of a plurality of predetermined speeds;
wherein actuation of the pressure sensor positioned in a lit footfall portion generates a first signal to the microprocessor assembly;
wherein actuation of the pressure sensor positioned in an unlit footfall portion generates a second signal to the microprocessor assembly;
wherein a null activation of the pressure sensor positioned in a lit footfall portion generates a second signal to the microprocessor assembly;

wherein the microprocessor assembly counts the respective first and second signal received;
wherein the microprocessor assembly generates a score based on the number of first and second signals received.

9. The apparatus of claim 8 and further comprising:
a flexible base layer;
a flexible, non-conducting electronics-mounting layer;
an impact-absorbent layer; and
a flexible top layer;
wherein the top layer includes grid markings outlining the array of footfall portions; and
wherein the at least one pressure sensor and the at least one light source are positioned in the electronics-mounting layer.

10. The apparatus of claim 9 and further comprising:
a first flexible spacing layer positioned between the electronics mounting layer and the impact-absorbent layer; and
a second flexible spacing layer positioned between the top layer and the impact-absorbent layer.

11. An electronic agility training system, comprising:
a first agility-training device, further comprising:
a first device array of multilayer, flexible footfall portions;
a first device microprocessor assembly operationally connected to the array of multilayer, flexible footfall portions;
a first device user interface operationally connected to the microprocessor assembly;
at least one first device pressure sensor positioned in each respective footfall portion and operationally connected to the microprocessor assembly;
at least one first device light source positioned in each respective footfall portion and operationally connected to the microprocessor assembly; and
a second agility training device operationally coupled to the first device and further comprising:
a second device array of multilayer, flexible footfall portions;
a second device microprocessor assembly operationally connected to the array of multilayer, flexible footfall portions;
at least one second device pressure sensor positioned in each respective footfall portion and operationally connected to the microprocessor assembly;
at least one second device light source positioned in each respective footfall portion and operationally connected to the microprocessor assembly;
wherein each respective microprocessor assembly is in electronic communication with the other respective microprocessor assembly;
wherein each respective microprocessor assembly is programmed to receive user information from a respective user interface;
wherein each respective microprocessor assembly is programmed to sequentially energize the light sources to light respective footfall portions in one of a plurality of predetermined patterns and at one of a plurality of predetermined speeds;
wherein actuation of the pressure sensor positioned in a lit footfall portion generates a first signal to a microprocessor assembly;
wherein actuation of the pressure sensor positioned in an unlit footfall portion generates a second signal to a microprocessor assembly;
wherein a null activation of the pressure sensor positioned in a lit footfall portion generates a second signal to a microprocessor assembly;

wherein a microprocessor assembly counts the respective first and second signal received;

wherein a microprocessor assembly generates a score based on the number of first and second signals received.

12. The system of claim 11 and further comprising at least one additional agility training device operationally connected to the first and second agility training devices.

13. The system of claim 11 and further comprising a second device user interface operationally connected to the microprocessor assembly.

14. The system of claim 11 wherein the microprocessors are connected in radio communication.

* * * * *